United States Patent
de Sousa Dias et al.

(10) Patent No.: US 9,090,581 B2
(45) Date of Patent: Jul. 28, 2015

(54) PROCESS FOR THE CONVERSION OF A CARBOHYDRATE-CONTAINING FEEDSTOCK

(75) Inventors: Ana Sofia Vagueiro de Sousa Dias, Amsterdam (NL); Gerardus Johannes Maria Gruter, Amsterdam (NL); Robert-Jan van Putten, Amsterdam (NL)

(73) Assignee: FURANIX TECHNOLOGIES B.V., Amsterdam (NL)

( * ) Notice: Subject to any disclaimer, the term of this patent is extended or adjusted under 35 U.S.C. 154(b) by 106 days.

(21) Appl. No.: 13/993,412

(22) PCT Filed: Dec. 28, 2011

(86) PCT No.: PCT/NL2011/050907
§ 371 (c)(1),
(2), (4) Date: Jul. 17, 2013

(87) PCT Pub. No.: WO2012/091570
PCT Pub. Date: Jul. 5, 2012

(65) Prior Publication Data
US 2013/0324708 A1    Dec. 5, 2013

Related U.S. Application Data

(60) Provisional application No. 61/427,588, filed on Dec. 28, 2010.

(30) Foreign Application Priority Data

Dec. 28, 2010  (NL) ..................................... 2005928

(51) Int. Cl.
| | |
|---|---|
| *C07H 15/04* | (2006.01) |
| *C07C 67/00* | (2006.01) |
| *C07D 307/58* | (2006.01) |
| *C07D 307/46* | (2006.01) |

(52) U.S. Cl.
CPC .............. *C07D 307/58* (2013.01); *C07C 67/00* (2013.01); *C07D 307/46* (2013.01); *C07H 15/04* (2013.01)

(58) Field of Classification Search
CPC ....... C07H 15/04; C07D 307/58; C07C 67/00
USPC .......................... 536/18.6; 549/479; 560/190
See application file for complete search history.

(56) References Cited

U.S. PATENT DOCUMENTS

| 2,917,537 A | 11/1957 | Haury | |
|---|---|---|---|
| 2009/0131690 A1* | 5/2009 | Gruter et al. .................. | 549/489 |

FOREIGN PATENT DOCUMENTS

| CN | 101400666 A | 4/2009 |
|---|---|---|
| CN | 101434589 A | 5/2009 |
| CN | 101475543 A | 7/2009 |
| CN | 101696226 A | 4/2010 |
| EP | 1834950 A1 | 9/2007 |
| EP | 2 090 573 A1 | 8/2009 |
| WO | 2007104514 A2 | 9/2007 |

OTHER PUBLICATIONS

Tarabanko et al. Sodium Hydrosulfate as the Catalyst for Carbohydrate Conversion into the Levulinic Acid and 5-Hydroxymetylfurfural Derivatives. J Siberian Fed University Chem 1:35-49, 2008.*
English Translation of a Chinese Office Action dated Jun. 6, 2014 for a counterpart foreign foreign application.

* cited by examiner

*Primary Examiner* — Brandon Fetterolf
*Assistant Examiner* — Yih-Horng Shiao
(74) *Attorney, Agent, or Firm* — Hoffmann & Baron, LLP

(57) ABSTRACT

A carbohydrate-containing feedstock is converted in a process by contacting the feedstock in a first step with an alcohol in the presence of a first acid catalyst at a temperature below 100° C. to yield an intermediate product, and contacting at least part of the intermediate product in a second step with an alcohol in the presence of a second acid catalyst at a temperature of at least 100° C. Products of such conversion may include hydroxymethylfurfural, hydroxymethylfurfural ethers, levulinic acid, esters thereof and furfural.

26 Claims, No Drawings

PROCESS FOR THE CONVERSION OF A CARBOHYDRATE-CONTAINING FEEDSTOCK

CROSS-REFERENCE TO RELATED APPLICATIONS

This application is the National Stage of International Application No. PCT/NL2011/050907, filed Dec. 28, 2011, which claims the benefit of U.S. Provisional Application No. 61/427,588, filed Dec. 28, 2010, and Netherlands Application No. NL 2005928, filed Dec. 28, 2010, the contents of which are incorporated by reference herein.

FIELD OF THE INVENTION

The present invention relates to a process for the conversion of a carbohydrate-containing feedstock. In particular it relates to a process wherein such a carbohydrate-containing feedstock is converted with an alcohol by dehydration. Products of such conversion may include hydroxymethylfurfural, hydroxymethylfurfural ethers, levulinic acid, esters thereof and furfural.

BACKGROUND OF THE INVENTION

A process wherein a carbohydrate-containing feedstock is dehydrated is known from WO2007/104514. In this known process a fructose- or glucose-containing starting material is contacted with an alcohol in the presence of an acid catalyst. The catalyst may be homogeneous or heterogeneous, e.g., a solid. This known process is of particular interest for the preparation of ethers of 5-hydroxymethylfurfural. The process is suitable for being conducted in a continuous mode. Thereto, a starting material comprising the carbohydrate and alcohol was fed to a reactor containing the acid catalyst. In the reactor the temperature was 125 to 300° C. This process was exemplified by experiments wherein about 10 grams of glucose or fructose-containing feedstock was dissolved per liter alcohol. Although the conversion and selectivity of the reaction was satisfactory, a drawback of this process is constituted by the limited solubility of the carbohydrate in the alcohol. Therefore, only diluted solutions of the carbohydrate in alcohol could be reacted in a continuous flow reactor without clogging the heterogeneous catalyst.

In U.S. Pat. No. 2,917,537 a process for the manufacture of levulinic acid and its esters has been described. In this process a carbohydrate is reacted with a lower alkanol and a non-reacting diluent in the presence of a strong acid catalyst at a temperature of 150 to 250° C. The diluent is insoluble in water and has a heat of vaporisation less than that of water and suitably less than that of the alkanol. It may be selected from a group consisting of hydrocarbons, chlorinated hydrocarbons, ethers and esters with an atmospheric boiling point below 190° C. In an example 100 pounds of sugar is mixed with 160 pounds of methanol and 240 pounds of benzene in the presence of one pound of sulphuric acid. It will be evident to the skilled person that the reaction mixture already initially comprises a dispersion of solid sugar in the methanol/benzene mixture. The mixture obtained is heated to 215° C. to carry out the conversion to the methyl ester of levulinic acid. The start of the process with such a dispersion makes it difficult to carry out the reaction in a continuous manner and impossible if the continuous process is conducted in a fixed bed reactor.

It is an object of the invention to provide a process wherein a carbohydrate-containing feedstock and an alcohol can be processed in one homogeneous phase, whilst the concentration of the carbohydrate-containing feedstock can be brought to a level that would make the conversion economically attractive.

It has now surprisingly been found that at temperatures below 100° C. a homogeneous solution of a carbohydrate in an alcohol in attractive concentrations can be obtained if the carbohydrate and the alcohol are present in a mixture that also comprises an acid catalyst.

SUMMARY OF THE INVENTION

Accordingly, the present invention provides a process for the conversion of a carbohydrate-containing feedstock, which process comprises contacting the feedstock in a first step with an alcohol in the presence of a first acid catalyst at a temperature below 100° C. to yield an intermediate product, and contacting at least part of the intermediate product in a second step with an alcohol in the presence of a second acid catalyst at a temperature of at least 100° C.

It is believed that during the first step the alcohol and the carbohydrate under the influence of the acid catalyst react to form a glycoside which tends to have a higher solubility in alcohol than the carbohydrate. Therefore, the concentration of such glycosides in an alcoholic solution that also contains an acid catalyst may be significantly higher than when the carbohydrate and the alcohol are mixed in the absence of acid catalyst. Since a carbohydrate solution is preferable over a carbohydrate heterogeneous suspension in the use of a continuous process, and since higher concentrations make a process economically more attractive, it is evident that the present invention provides a significant advantage over the prior art. In accordance with the IUPAC definition a glycoside is any molecule in which a carbohydrate group is bonded through its anomeric carbon to another group via a glycosidic bond. The carbohydrate group is known as the glycone and the alcohol group as the aglycone or genin part of the glycoside. The glycone can consist of a single sugar group (monosaccharide) or several sugar groups (oligosaccharide).

DETAILED DESCRIPTION OF THE INVENTION

The temperature of the first step is below 100° C. In order to promote the formation of glycosides the temperature is preferably at least 10° C., more preferably from 30 to 80° C. In this temperature range the formation of glycosides can easily take place, whereby a concentration of carbohydrate-derived material in the alcoholic solution can be enhanced. At these low temperatures the conversion of the carbohydrate by dehydration to a product comprising hydroxymethylfurfural, levulinic acid or their derivatives substantially does not take place. When the first step is conducted at atmospheric pressure the temperature is preferably at most the boiling temperature of the alcohol that is being used. That means that, typically, the conversion of the carbohydrate to furan derivatives or levulinic acid or its derivatives does not take place. It will be evident that when the desired temperature lies beyond the atmospheric boiling point of the alcohol elevated pressures may be applied. Suitable pressures for the first step, therefore, range from 1 to 5 bar.

The duration of the first step is not critical. The temperature and the duration may be varied to arrive at the desired conversion to glycosides to accomplish complete dissolution and the desired concentration level. The duration is further dependent on the nature of the carbohydrate, the amount of the first acid catalyst, the nature of the acid catalyst, presence and, if so, the amount of a diluent, and the stifling speed. When the carbohydrate-containing feedstock is already a liquid, e.g., a syrup, such as High Fructose Corn Syrup, the addition of an alcohol might lead to precipitation of the carbohydrate. By the additional admixing of an acid to the mixture of such a liquid feedstock and alcohol, the acid catalyzed formation of glycosides prevents crystallization of the carbohydrate after alcohol addition. The contact time of the carbohydrate-containing feedstock and the alcohol with the first acid catalyst in the first step may last as long as feasible, but is suitably at most 12 hours. This allows the formation of a homogeneous solution. Evidently, the skilled person may want to attempt to make the contact time as short possible. Good results are obtained when the contact time is at least 0.1 hr. Therefore, the contact time of the carbohydrate-containing feedstock and the alcohol with the first acid catalyst advantageously ranges from 0.1 to 12 hr.

The carbohydrate-containing feedstock may be selected from a variety of possible feedstocks. Hence it is possible to use agricultural raw materials or other biomass resources. The carbohydrate-containing feedstock may comprise mono-, di-, oligo- or polysaccharides. The components of particular interest in biomass are those feedstocks that contain a monosaccharide. Examples of suitable monosaccharides include fructose and mixtures of fructose with other monosaccharides, such as other hexoses and/or pentoses. A hexose is a monosaccharide with six carbon atoms having the chemical formula $C_6H_{12}O_6$. Hexoses may be classified by functional group, with aldohexoses having an aldehyde at position 1, and ketohexoses having a ketone at position 2. Fructose is a ketohexose. Suitable other hexoses include but are not limited to glucose, galactose, mannose, and their oxidized derivatives, e.g. aldonic acid, reduced derivatives, e.g. alditol, etherified, esterified and amidated derivatives. A pentose is a monosaccharide with five carbon atoms, having the chemical formula $C_5H_{10}O_5$. They may either have an aldehyde functional group in position 1 (aldopentoses), or a ketone functional group in position 2 (ketopentoses). Suitable 5-carbon monosaccharides include but are not limited to arabinose, ribose, ribulose, xylose, xylulose and lyxose.

The di- and oligosaccharide carbohydrates containing more than one saccharide unit, are suitably hydrolysed in the alcohol, resulting in a mixture of dissolved di- and/or oligosaccharides, monomeric saccharide units and/or glycoside units. Examples of suitable disaccharides include maltose, lactose, trehalose, turanose and sucrose, sucrose being preferred. Sucrose is abundantly available and therefore very suitable. The disaccharides can easily be converted into the monomeric units. Examples of suitable oligosaccharide are fructo-oligosaccharides which are found in many vegetables. By oligosaccharides is understood a carbohydrate that is built up of 3 to 10 monosaccharide units. Polysaccharides have more than ten monosaccharide units. These are polymeric structures formed of repeating units joined together by glycosidic bonds. The number of monosaccharide units in a polysaccharide may vary widely, and may range from 10 to 3000. Suitable polysaccharides include fructan, i.e. a polymer of fructose moieties, and levan, which is composed of D-fructofuranosyl moieties. Mixtures may also be used. Starch, hemi-cellulose and in particular cellulose are not very suitable starting materials for the first step as they will not be easily hydrolyzed under the mild conditions applied in the first step. However, hydrolysis process streams from enzymatic or catalytic hydrolysis of starch, cellulose and hemi-cellulose or from alcoholysis processes that already contain mono- and disaccharides can suitably be used as starting feedstock for the first step. In view of the above, the preferred monosaccharide is fructose, glucose and mixtures thereof. The preferred disaccharide is sucrose.

The carbohydrate-containing feedstock may comprise compounds other than carbohydrates. Such compounds include 5-hydroxymethylfurfural, 5-alkoxymethylfurfural, furfural, levulinic acid and alkyl levulinates. However, preferably, the carbohydrate is the major component of the carbohydrate-containing feedstock. Suitably, the carbohydrate-containing feedstock comprises from 50 to 100% wt of carbohydrate, based on the weight of the carbohydrate-containing feedstock. More preferably, the carbohydrate-containing feedstock essentially consists of carbohydrate.

In glycoside formation one monosaccharide unit reacts with one alcohol molecule whilst releasing water. It is therefore preferred that the molar amount of alcohol is greater than the molecular equivalent of carbohydrates, wherein the molecular equivalent refers to the molar amount of monosaccharide units. Typically, there may be a large excess of alcohol. Suitably, the carbohydrate-containing feedstock is present in an amount ranging from 10 to 50 wt % for the carbohydrates, based on the total amount of carbohydrate and alcohol. When the carbohydrate is fructose, the amount suitably ranges from 20 to 50 wt %.

The alcohol serves as solvent and as reactant. Carbohydrates tend to be more soluble in polar solvents than in apolar solvents. Since smaller alcohols are more polar than larger alcohols it is preferred to use alcohols that contain from 1 to 6 carbon atoms. The smaller alcohols also react faster than the larger alcohols to form glycosides, which makes it further advantageous to use these alcohols. The alcohol may be aliphatic or aromatic, and may be linear, branched or cyclic. It may also comprise one or more heteroatoms. However, it is preferred to use alkanols, which may be linear or branched. Therefore, the preferred alcohols are alkanols having from 1 to 6 carbon atoms. Examples include methanol, ethanol, n-propanol, i-propanol, n-butanol, i-butanol, butanol-2, t-butanol, n-pentanol, n-hexanol and mixtures of two or more of these alcohols. Since the most polar solvents that enable the highest concentrations, are the alkanols with the fewest carbon atoms, the most preferred alkanols are methanol, ethanol and mixtures thereof.

If desired, the mixture of carbohydrate-containing feedstock and alcohol may contain one or more added diluents. Thus, in addition to water that is formed in the first and second step, preferably a diluent is added to the first and/or second step. Suitable diluents comprise water, sulphoxides, such as DMSO, ketones, such as acetone, ethyl methyl ketone, isobutyl methyl ketone and mixtures thereof. Water is a preferred diluent. Water is a good solvent for carbohydrates. That constitutes one reason for the preference for water. Further, the conversion of carbohydrates to glycosides will result in the formation of water. The preference for water has as additional advantage that the carbohydrate-containing feedstock, the alcohol or any other compound that is present, does not need to be extensively dried. This makes the process more economical. Suitable ratios between alcohol and diluent vary from 100:1 to 1:1 w/w, preferably from 50:1 to 2:1 w/w, more preferably from 40:1 to 3:1 w/w.

The first step is to be conducted in the presence of a first acid catalyst. Suitably the carbohydrate-containing feedstock and the alcohol are mixed together with a first acid catalyst, that is soluble in the mixture, to form a homogeneous solution. Suitable homogeneous catalysts include mineral acids such as sulphuric acid, hydrochloric acid, nitric acid, phosphoric acid and phosphorous acid. It is also possible to use Lewis acids such as boron trifluoride. Organic acids are also suitable, e.g. trifluoroacetic acid, alkyl sulphonic acids, such as methanesulphonic acid, alkylbenzenesulphonic acid, such as p-toluene-sulphonic acid, and alkylnaphthalene-sulphonic acids and mixtures thereof. Since good results are obtainable with sulphuric acid, this acid is preferred as homogeneous first acid catalyst.

The amount of such a homogeneous first acid catalyst is preferably a sub-stoichiometric amount, based on the carbohydrate-containing feedstock. Typically, the amount of homogeneous first acid catalyst ranges from 0.01 to 40 mole %, based on the carbohydrate in the feedstock. Preferably, the catalyst is present in an amount of 0.05 to 20 mole %, more preferably from 0.1 to 10 mole %.

Alternatively, the first acid catalyst in the first step is a heterogeneous catalyst, i.e. a catalyst in a different phase from the liquid alcohol. The heterogeneous first acid catalyst is advantageously a solid catalyst. Suitably, the solid catalyst is selected from the group consisting of solid organic acids, solid inorganic acids, acidic ion exchange resins, silica-alumina, clays, zeolites and combinations thereof. Clays such as montmorillonite, can suitably be used. Due to the mild temperature conditions in the first step, acidic ion exchange resins, such as strong acidic, sulphonic acid, macroreticular polymeric resins based on cross-linked copolymers of styrene and divinylbenzene can also be used. Preferred resins include the Amberlyst resins available from Rohm & Haas. Preferably, the solid catalysts comprise a zeolite or an acidic ion exchange resin to which organic acids have been immobilised. The zeolite has preferably been subjected to ion exchange with ammonia or an ammonium compound to reduce the number of metal ions in the zeolite. After ion exchange with ammonium ions, zeolite is calcined to yield the H-form of the zeolite which has an acid character. The zeolite, which is an aluminosilicate, is preferably chosen from the group consisting of mordenite, faujasite, such as zeolite X or Y, MCM-41 type zeolite, zeolite beta, ZSM-5, ZSM-11, ZSM-12 and mixtures thereof. Preferably, the zeolite is a faujasite, such as zeolite Y.

The first acid catalyst may also be chosen from Lewis acids. Suitable Lewis acid catalysts include salts such as $CrCl_2$, $CuCl$, $CuCl_2$, $MoCl_3$, $FeCl_3$, $CrCl_3$ or $VCl_3$. Preferably, the metal salts are used as such. Alternatively, one may use an ionic liquid, suitably comprising an imidazolium or pyridinium chloride that is prepared by allowing the reaction between an imidazolium chloride or pyridinium chloride with a metal chloride, such as $CrCl_2$, $CuCl$, $CuCl_2$, $MoCl_3$, $FeCl_3$, $CrCl_3$ or $VCl_3$. The ionic liquids thus obtained can be immobilised by allowing the metal chloride to react with a suspension of a silica wherein the silica is reacted with an alkoxysilyl-imidazolinium or pyridinium chloride.

In view of the above, the first acid catalyst is suitably a homogeneous or heterogeneous catalyst. The homogeneous catalyst is preferably a mineral acid, such as sulphuric acid, and the heterogeneous catalyst is preferably selected from the group consisting of zeolites and acidic ion exchange resins, such as zeolite Y, ZSM-12, and sulphonic moieties-containing acidic resins.

The first acid catalyst may be added to the mixture of alcohol and carbohydrate-containing feedstock. Due to the catalytic activity of the catalyst any solid undissolved carbohydrate will be converted into a glycoside that will dissolve. That applies to both a homogeneous acid catalyst and a heterogeneous acid catalyst. In case of heterogeneous catalysts, a slurry of carbohydrate-containing feedstock and alcohol is contacted with a solid catalyst, typically contained in a so-called basket, to achieve dissolution by a certain level of conversion into glycoside. The carbohydrate solution may be separated from the solid catalyst, leaving the solid acid catalyst behind or, optionally, more carbohydrate may be added to achieve a higher concentration of carbohydrate than the one in the initial mixture.

As indicated above, the mixture of carbohydrate-containing feedstock and alcohol may contain one or more added diluents. Water is a preferred diluent. The diluent may be present in the first step and/or in the second step. Typically the diluent is added as an alcohol/diluent mixture in the first step.

The first step results in the formation of an intermediate product. The intermediate product is contained in the effluent from the first step. As indicated above, it is believed that the intermediate product comprises glycosides. Therefore, the effluent contains the intermediate product, i.e. the carbohydrate and/or glycoside, and further alcohol, water, formed as by-product of the glycoside formation, and optionally diluent. Typically, the intermediate product comprises 10 to 100 mol % of glycosides, based on the number of moles of carbohydrates in the carbohydrate-containing feedstock. It is not necessary that all carbohydrates of the feedstock are converted to glycosides. The intermediate product may comprise glycosides and also original carbohydrate from the feedstock. Since the solubility of glycosides is enhancing the solubility of the feedstock, the intermediate product suitably comprises 50 to 95 mol % glycosides, based on the number of moles of the carbohydrate in the carbohydrate-containing feedstock. It is possible to only use part of the intermediate product as feed for the second step. However, preferably, the entire intermediate product is passed as feed to the second step.

It is also possible to remove part or all of one or more of the components of the effluent containing the intermediate product, and pass the remainder as feed to the second step. Hence, it is possible to extract some water from the intermediate product. Alternatively or in addition, when a different diluent is used, also at least part of the diluent may be extracted. Also, if desired, the solid first acid catalyst, when used, may be separated or the homogeneous first acid catalyst, when used, may be neutralized by addition of up to a stoichiometric amount of base after which a different acid catalyst can be used for the second step. Preferably, a homogeneous catalyst that is contained in the intermediate product-containing effluent is transferred to the second step. Advantageously, substantially the entire intermediate product-containing effluent from the first step, containing also the alcohol of the first step, is subjected to the temperature and pressure conditions of the second step.

The second step is carried out at a temperature of at least 100° C. Suitable temperatures for the second step range from 105 to 300° C., more preferably from 150 to 280° C., most preferably from 175 to 250° C. The pressure may also vary. The reaction of the first step is typically conducted at atmospheric pressure, whereas for the second step, preferably, elevated pressures are employed as this step is typically performed at temperatures above the boiling point of the alcohol or the boiling point of alcohol/diluent mixtures, for example a methanol/water mixture. The pressure may depend on the temperature and the alcohol used. Whereas for the first step suitable pressures range from 1 to 5 bar, the pressure for the second step is preferably in the range of from 2 to 150 bar, more preferably from 10 to 120 bar, most preferably from 20 to 80 bar.

The second acid catalyst of the second step may be the same as the first acid catalyst of the first step. Hence, all catalysts described above may also be used in the second step. Accordingly, the second acid catalyst in the second step is advantageously a heterogeneous or homogeneous catalyst. Suitable homogeneous catalysts include mineral acids, Lewis acids and organic acids, as described above. Suitably, the heterogeneous second acid catalyst is selected from the group consisting of solid organic acids, solid inorganic acids, acidic ion exchange resins, zeolites and combinations thereof. The homogeneous second acid catalyst is preferably a mineral acid, such as sulphuric acid, and the heterogeneous catalyst is preferably selected from the group consisting of solid Lewis acids and zeolites. It is emphasised that the first and second acid catalysts in the first and second step need not be the same. Therefore, different catalysts from the groups mentioned above may be used in the second step. Preferred are sulphuric acid as homogeneous second acid catalyst and Lewis acids and zeolites as heterogeneous catalyst. The preferred Lewis acids and zeolites are as described above in connection with the first step. It is also found very convenient to use the same catalyst in both steps. Therefore, the use of a homogeneous acid catalyst as both the first and the second acid catalyst is very advantageous.

The process of the present invention has two steps that may be performed in different reactors. Either one of the steps may be performed in a continuous or in a batch-type fashion. The first step can be performed in either batch or continuous mode. This step is less critical than the second step. When the first step is performed in a batch reactor, the contact time of the reactants advantageously ranges from 0.1 to 12 hours. When the first step is performed in a continuous mode, it may be carried out in a continuous stirred tank reactor (CSTR), a plug flow reactor, or a static mixer comprising baffles arranged in a housing, wherein a plug flow reactor and a CSTR are preferred. Especially when a homogeneous catalyst is used in the first step, a static mixer can suitably be used as a reactor for this step. In a continuous reactor the contact time is typically in the range of from 0.1 to 12 hours.

The second step is preferably performed in a continuous mode. Thereto, when a homogeneous catalyst is employed, suitably a continuous stirred tank reactor (CSTR) or a plug-flow reactor may be used, wherein the plug flow reactor is preferred. When the second step is performed with a heterogeneous acid catalyst, typically a fixed bed reactor is used. When the second step is performed in a continuous reactor, the reactor of the first step can be a batch reactor, a CSTR or a plug-flow reactor. The residence time in the second step may suitably vary from 30 s to 2 hours, preferably from 1 min to 1 hour. When the second step is conducted in a plug flow reactor, the liquid hourly space velocity ranges from 0.1 to 1,000 or more preferably from 1 to 100 $hr^{-1}$.

In the most preferred configuration, the reactors of the first and the second step are integrated into one set-up. As the reactor temperature of the second step is higher than the reactor temperature of the first step, the two reactors may typically be connected via a heat exchanger.

The process of the present invention can suitably be used for the conversion of carbohydrates to hydroxymethylfurfural, derivatives thereof, levulinic acid, derivatives thereof and/or furfural. By using alcohols as solvent and reactant the derivatives will be the ethers of hydroxymethylfurfural and the esters of levulinic acid. When water is used as a diluent at the start of the first step and dependent on the amount of water formed in the processes of the first and the second step, amounts of 5-hydroxymethylfurfural and levulinic acid will be present in the product of the second step in addition to the ether of 5-hydroxymethylfurfural and levulinic acid ester. It depends also on reaction conditions, in particular acid strength, nature and amount of carbohydrate, what the major product will be.

Hydroxymethylfurfural, ethers of hydroxymethylfurfural, levulinic acid, levulinic acid esters and furfural are useful starting materials for various chemical compounds, e.g. furan-dicarboxylic acid that may be used in the preparation of polyesters. The compounds may also be used as fuel or fuel additives.

The present invention will be further elucidated by means of the following examples.

EXAMPLES

Example 1

In a reaction vessel 250 gr (1.39 mol) of fructose in 700 mL methanol was stirred at room temperature overnight, i.e. for about 10 hrs, in the presence of 5.6 mmol of sulphuric acid at atmospheric pressure. A homogeneous solution was obtained. Almost all of the fructose was converted to methyl fructoside ("Me-Frc"). Subsequently, a methanol/water mixture was added until 1.0 L of a homogeneous clear solution was obtained. At a flow of 1 mL/min the resulting solution was passed through a plug flow type reactor that was heated to different temperatures. The pressure of this step was kept at 62 bar. The residence time in the heated zone of the reactor was 120 s. The results of the combined first and second step are shown in Table 1. In the Table the yield is calculated according to the expression: $Y(P)=100*n_tP/n_iS$, where $Y(P)$ is the yield of product P, $n_iS$ is the initial number of moles of the substrate fructose and $n_tP$ is the number of moles of the product P at a reaction time t. "Me-Frc" means methyl fructoside, "HMF" is 5-hydroxymethylfurfural, "MMF" is methoxymethyl furfural, and "Me-Lev" is methyl levulinate.

TABLE 1

| Temp., °C. | Conversion, % | Me-Frc yield, % | HMF yield, % | MMF yield, % | Furfural yield, % | Me-Lev yield, % |
|---|---|---|---|---|---|---|
| 160 | 96 | 33 | 11 | 8 | 1 | 0.9 |
| 180 | 98 | 10 | 20 | 27 | 2 | 3.2 |
| 200 | 100 | 0 | 18 | 51 | 2 | 7.3 |
| 220 | 100 | 0 | 6 | 60 | 2 | 12.4 |

Example 2

In a reaction vessel a certain amount of fructose (260, 350 or 500 g) was stirred at 60° C. for 4 hours in the presence of 5.6 mmol of sulphuric acid and 700 mL of a mixture of methanol and water (5% vol water). The mixture was cooled down and a methanol/water mixture was added until 1.0 L of a homogeneous, clear solution was obtained. This solution contains a mixture of fructose ("Fruc") and methyl fructosides ("Me-Frc"). The resulting mixture was pumped, in a second step, into a plug flow type reactor that was heated at a certain temperature (180, 200 or 220° C.). The pressure in this step was kept at 65 bar. The results are shown in Table 2, wherein yield is as discussed above and the products include methoxymethylfurfural ("MMF") and methyl levulinate ("Me-Lev").

TABLE 2

| First step | | | Second step | | | | | |
|---|---|---|---|---|---|---|---|---|
| Fruc (g/L) | Me-Frc yield, % | Residence time (s) | Temp., °C. | Conversion, % | HMF yield, % | MMF yield, % | Furfural yield, % | Me-Lev yield, % |
| 260 | 64 | 120 | 220 | 100 | 13 | 57 | 3 | 9 |
| 350 | 46 | 180 | 200 | 100 | 16 | 50 | 2 | 12 |
| 500 | 45 | 240 | 180 | 96 | 26 | 31 | 1 | 7 |

Comparative Example 1

Fructose in different amounts was mixed at room temperature with 1 liter of a methanol-water mixture (5% vol water) without the addition of sulphuric acid.

At 500 g fructose per liter, no homogeneous solution was obtained.

At 350 g/l, no homogeneous solution was obtained.

At 260 g/l, no homogeneous solution was obtained. Since no homogeneous solutions but slurries were obtained, these slurries would result in direct blockage in the reactor and would lead to no reaction with a heterogeneous catalyst.

These experiments show that without acid catalyst concentrated solutions of carbohydrate in alcohol cannot be obtained.

Example 3

An amount of 200 g fructose was added to 800 mL of a mixture of methanol and water (5 vol % water) that contained 55 mmol (5.4 gr) sulphuric acid. The admixture obtained was stirred at 60° C. until all solids were dissolved in about 2 hours. The solution was cooled down and a methanol/water mixture (5 vol % water) was added until 1.0 L of an homogeneous, clear solution was obtained. After dissolving the fructose the solution obtained was passed through a plug flow reactor that was heated at different temperatures, varying from 180 to 220° C. The residence time in the heated zone of the reactor was also varied and was set at 2 or 4 minutes. The pressure in this step was maintained at 65 bar. After having obtained a steady state condition in the reactor the product stream was analysed. The analysis determined the conversion (1 minus the number of moles of fructose in the product stream divided by the number of moles of fructose in the starting material, expressed in percent), and the yields for 5-hydroxymethylfurfural (HMF), 5-methoxymethylfurfural ("MMF"), methyllevulinate ("Me-Lev") and levulinic acid ("LA"). The yield is expressed in percent and has been calculated as the number of moles of the compound in question divided by the initial amount of moles of fructose times 100. The results are shown in Table 3.

TABLE 3

| Temp., °C. | Residence time, min | Conversion % | Yield HMF, % | Yield MMF, % | Yield Me-Lev, % | Yield LA, % |
|---|---|---|---|---|---|---|
| 180 | 2 | 99.8 | 6.9 | 55.6 | 19.3 | 1.9 |
| 180 | 4 | 100 | 2.9 | 43.5 | 30.7 | 2.6 |
| 200 | 2 | 99.9 | 2.8 | 46.8 | 28.3 | 2.7 |
| 220 | 2 | 99.9 | 1.1 | 23.2 | 44.0 | 4.1 |
| 220 | 4 | 99.9 | 0.8 | 15.0 | 52.2 | 5.0 |

Example 4

To show that the product slate can be influenced by the reaction conditions, the following experiments were conducted.

The experiments as described in Example 3 were repeated but with 100 gram of HMF or MMF as feedstock instead of fructose. This feedstock mimics the products of the conversion of fructose to HMF and ethers thereof. These feedstocks were dissolved in 1 liter of a mixture of methanol and water (5 vol % water) that contained 55 mmol (5.4 gr) sulphuric acid. The pressure was 65 bar. Other reaction conditions and the results of these experiments are shown in Table 4. The conversion and the yields were calculated in the same way as in Example 3, but based on the respective feedstock.

TABLE 4

| Substr. | Temp, °C. | Res. time, min. | Conversion, % | Yield HMF, % | Yield MMF, % | Yield Me-Lev, % | Yield LA, % |
|---|---|---|---|---|---|---|---|
| HMF | 180 | 2 | 98.8 | — | 58.2 | 40.1 | 1.0 |
| HMF | 200 | 2 | 99.4 | — | 34.6 | 52.6 | 1.7 |
| HMF | 200 | 4 | 99.6 | — | 22.0 | 63.7 | 1.9 |
| HMF | 220 | 2 | 99.6 | — | 20.7 | 71.3 | 2.2 |
| HMF | 220 | 4 | 99.7 | — | 13.1 | 75.2 | 2.8 |
| MMF | 180 | 2 | 49.9 | 0.4 | — | 48.5 | 1.7 |
| MMF | 200 | 2 | 68.0 | 0.2 | — | 61.2 | 2.3 |
| MMF | 200 | 4 | 75.8 | 0 | — | 67.9 | 2.5 |
| MMF | 220 | 2 | 80.7 | 0 | — | 74.1 | 2.7 |
| MMF | 220 | 4 | 86.1 | 0 | — | 76.4 | 3.1 |

Example 5

An amount of 100 g glucose was added to 800 mL of a mixture of methanol and water (5 vol % water) that contained 55 mmol (5.4 gr) sulphuric acid. The admixture obtained was stirred at 60° C. until all solids were dissolved in about 4 hours. After the dissolution, the volume of the solution is adjusted to 1 L by adding a mixture of methanol and water (5 vol % water). The solution obtained which contains a mixture of glucose and glucosides was passed through a plug flow reactor that was heated at different temperatures, varying from 200 to 220° C. The residence time in the heated zone of the reactor was also varied and was set at 2, 4 or 8 minutes. The pressure in the reactor was maintained at 65 bar. After having obtained a steady state condition in the reactor the product stream was analysed. The analysis determined the conversion (1 minus the number of moles of glucose and glucosides in the product stream divided by the number of moles of glucose in the starting material, expressed in percent), and the yields for 5-hydroxymethylfurfural ("HMF"), 5-methoxymethylfurfural ("MMF"), methyllevulinate ("Me-Lev") and levulinic acid ("LA"). The yield is expressed in percent and has been calculated as the number of moles of the compound in question divided by the initial moles of glucose times 100. The results are shown in Table 5.

TABLE 5

| Temp., °C. | Residence time, min | Conversion, % | Yield HMF, % | Yield MMF, % | Yield Me-Lev, % | Yield LA, % |
|---|---|---|---|---|---|---|
| 200 | 2 | 18.5 | 0.1 | 3.2 | 3.2 | 0.0 |
| 200 | 4 | 33.5 | 0.1 | 4.7 | 7.3 | 0.0 |
| 220 | 4 | 69.2 | 1.4 | 11.4 | 20.2 | 1.0 |
| 220 | 8 | 80.0 | 1.2 | 11.4 | 23.7 | 1.2 |

Comparative Example 2

Glucose in different amounts was mixed with 1 liter of a methanol-water mixture (5% vol water) without the addition of sulphuric acid.

At 100 g glucose per liter, no homogeneous solution was obtained.

At 50 g/l, no homogeneous solution was obtained. Since no homogeneous solutions but slurries were obtained, these slurries would result in direct blockage in the reactor and would lead to no reaction with a heterogeneous catalyst.

These experiments show that without acid catalyst, concentrated solutions of carbohydrate in alcohol cannot be obtained.

Example 6

An amount of 200 g fructose was added to 800 mL of a mixture of methanol and water (5 vol % water) and 20 g of Amberlyst 15, i.e. a strongly acidic, sulphonic acid, macroreticular polymer resin based on styrene and divinylbenzene from Rohm and Haas, in a catalyst basket was introduced into a reactor vessel. The admixture obtained was stirred at 60° C. until all solid fructose was dissolved in about 3 hours. After the dissolution, the catalyst basket was removed and the volume of the solution was adjusted to 1 L by adding a mixture of methanol and water (5 vol % water). The solution obtained which contains a mixture of fructose and fructosides was passed through a fixed bed plug flow reactor containing ZSM-12 solid acid catalyst in protonated form using a LHSV of 12.5 hr$^{-1}$ at a temperature of 180° C. The pressure in this step was maintained at 65 bar. After having obtained a steady state condition in the reactor for 12 hours, the product stream was analysed. The analysis determined the conversion (1 minus the number of moles of fructose and fructosides in the product stream divided by the number of moles of fructose in the starting material, expressed in percent), and the yields for 5-hydroxymethylfurfural ("HMF"), 5-methoxymethylfurfural ("MMF"), furfural ("F"), methyllevulinate ("Me-Lev") and levulinic acid ("LA"). The yield is expressed in percent and has been calculated as the number of moles of the compound in question divided by the initial moles of fructose times 100. The results are shown in Table 6.

TABLE 6

| Temp °C. | LHSV | Conversion % | Yield HMF, % | Yield MMF, % | Yield F, % | Yield Me-Lev, % | Yield LA, % |
|---|---|---|---|---|---|---|---|
| 180 | 12.5 | 91.0 | 1.8 | 30.6 | 12.2 | 19.9 | 2.5 |

The invention claimed is:

1. A process for dehydrating a carbohydrate-containing feedstock, wherein the process comprises:
   contacting the feedstock in a first step with an alcohol, selected from the group consisting of methanol, ethanol and a mixture thereof, in a presence of a first acid catalyst at a temperature below 100° C. to yield an intermediate product; and contacting at least part of the intermediate product in a second step with a second alcohol, selected from the group consisting of methanol, ethanol and a mixture thereof, in a presence of a second acid catalyst at a temperature ranging from 105 to 300° C.

2. The process according to claim 1, wherein the first step is carried out at a temperature of at least 10° C.

3. The process according to claim 1, wherein the carbohydrate-containing feedstock and the alcohol are contacted with the first acid catalyst in the first step during a contact time which ranges from 0.1 to 12 hr.

4. The process according to claim 1, wherein the carbohydrate is selected from the group consisting of monosaccharides, disaccharides, oligosaccharides and polysaccharides.

5. The process according to claim 4, wherein the disaccharide is sucrose.

6. The process according to claim 4, wherein the monosaccharide is fructose, glucose or a mixture thereof.

7. The process according to claim 1, wherein the carbohydrate-containing feedstock comprises from 50 to 100% wt of carbohydrate, based on the carbohydrate-containing feedstock.

8. The process according to claim 1, wherein in addition to water that is formed in the first and second steps, a diluent is added to the first and/or second steps.

9. The process according to claim 8, wherein the diluent is water.

10. The process according to claim 8, wherein the alcohol and added diluent are present in a weight ratio that varies from 50:1 to 0.1:1 w/w.

11. The process according to claim 1, wherein the first acid catalyst is a homogeneous catalyst.

12. The process according to claim 1, wherein the first acid catalyst is a heterogeneous catalyst.

13. The process according to claim 1, wherein the second acid catalyst is a homogeneous catalyst.

14. The process according to claim 1, wherein the second acid catalyst is a heterogeneous catalyst.

15. The process according to claim 1, wherein the first and the second acid catalysts are the same.

16. The process according to claim 1, wherein the second step is carried out at a temperature ranging from 150 to 280° C.

17. The process according to claim 1, wherein at least the second step is carried out in a continuous mode.

18. The process according to claim 17, wherein the continuous mode is carried out in a continuous stirred tank reactor, a plug flow reactor or a fixed bed reactor.

19. The process according to claim 17, wherein the continuous mode is carried out at a liquid hourly space velocity from 0.1 to 1,000 hr$^{-1}$.

20. The process according to claim 2, wherein the first step is carried out at a temperature ranging from 30 to 80° C.

21. The process according to claim 10, wherein the alcohol and added diluent are present in a weight ratio that varies from 20:1 to 1:1 w/w.

22. The process according to claim 11, wherein the first acid catalyst is a mineral acid.

23. The process according to claim 12, wherein the first acid catalyst is selected from the group consisting of zeolites and acidic ion exchange resins.

24. The process according to claim 13, wherein the second acid catalyst is a mineral acid.

25. The process according to claim 14, wherein the second acid catalyst is selected from the group consisting of zeolites and acidic ion exchange resins.

26. The process according to claim 19, wherein the continuous mode is carried out at a liquid hourly space velocity from 1 to 100 hr$^{-1}$.

* * * * *